United States Patent [19]

Haoli

[11] 4,422,968

[45] Dec. 27, 1983

[54] β-ENDORPHIN ANALOGS

[75] Inventor: Choh Haoli, Berkeley, Calif.

[73] Assignee: The Regents of the University of California, Berkeley, Calif.

[21] Appl. No.: 416,998

[22] Filed: Sep. 13, 1982

[51] Int. Cl.$^3$ ............................................. C07C 103/52
[52] U.S. Cl. ............................................. 260/112.5 E
[58] Field of Search ................................. 260/112.5 E

[56] References Cited

U.S. PATENT DOCUMENTS

| Re. 29,842 | 11/1978 | Li | 260/112.5 E |
| 4,081,434 | 3/1978 | Li | 260/112.5 E |
| 4,116,950 | 9/1978 | Li | 260/112.5 E |

*Primary Examiner*—Delbert R. Phillips
*Attorney, Agent, or Firm*—Jon S. Saxe; Bernard S. Leon; George M. Gould

[57] ABSTRACT

The novel β-endorphin analog [D-Ala$^2$, Phe$^3$, Gly$^4$, Tyr$^5$, Pro$^6$]-β-endorphin has been synthesized and has been found to be the most potent analog of β-endorphin yet developed for inducing analgesia.

3 Claims, No Drawings

β-ENDORPHIN ANALOGS

This invention was made with Government support under Grant No. MH 30245 awarded by the Dept. of Health and Human Services. The Government has certain rights in this invention.

BACKGROUND OF THE INVENTION

The isolation of β-endorphin from mammalian brain and pituitary extracts has been described in the art. See for example U.S. Pat. No. 4,038,222 reissued as U.S. Pat. No. RE 29,842. The availability of synthetic methods for preparing β-endorphin has allowed studies into structure-activity relationship with analogs of β-endorphin.

Modifications have been made in the amino terminal or enkephalin portion of the molecule, i.e., (1–5) β-endorphin. Similar modifications made in enkephalin had produced enkephalin analogs with substantially enhanced analgesic activity over that of the parent compound. However, the β-endorphin analogs with few exceptions such as, for example [D-Ala$^2$]-β-endorphin, did not have the level of activity of the parent compound. See in this regard Yamashiro et al., Int. J. Pept. Prot. Res. 10, 159 (1977). Analogs which are modified in both the amino and carboxy terminal sequences are described in U.S. Pat. No. 4,116,950. Again all compounds which have modifications in the enkephalin region (1–5) exhibit reduced analgesic potency compared to β-endorphin.

Thus as seen above efforts to increase the analgesic potency of β-endorphin by entrapolating findings on enkephalin analogs to the β-endorphin case have generally not been successful. Note also Li in *Hormonal Proteins and Peptides* X pp. 1–34 (Academic Press, New York 1981). The most potent enkephalin analogs have resulted from changes in both positions 2 and 5. As an example, [D-Ala$^2$, D-Leu$^5$]-enkephalin has been reported to be almost equipotent with $\beta_c$-endorphin as an analgesic. See Wei et al., Life Sci. 21 321 (1977). However, [D-Ala$^2$, D-Leu$^5$]-$\beta_h$-endorphin has only 8% of the activity of $\beta_h$-endorphin as reported by Yamashiro et al. Int. J. Pep. Prot. Res. 11, 251 (1978).

It has recently been reported that dermorphin, a heptapeptide of the sequence H-Tyr-D-Ala-Phe-Gly-Tyr-Pro-Ser-NH$_2$, isolated from the skin of the South American frog *Phyllomedusa sauvege* has potent analgesic properties. See Montecucchi et al. Int. J. Pep. Prot. Res. 17, 275 (1981). Broccardo et al. Br. J. Pharmacol. 73, 625 (1981) have reported that dermorphin is 752 times more active than morphine in a rat tail-flick assay. For comparison camel β-endorphin is about 33 times more active than morphine in the same assay as reported by Lok et al., Proc. Natl. Acad. Sci. USA 73, 2895 (1976).

DESCRIPTION OF THE INVENTION

The present invention relates to analogs of β-endorphin which are substituted in the amino terminal and which unexpectedly exhibit substantially enhanced analgesic activity when compared to the parent β-endorphin molecule and increased stability compared to the dermorphin molecule.

The analogs of the present invention can be represented by the formula [D-Ala$^2$, Phe$^3$, Gly$^4$, Tyr$^5$, Pro$^6$]-β-endorphin wherein the β-endorphin molecule can have the sequence of the human, porcine or ovine (camel) variations.

The compounds of the invention can be conveniently prepared by utilizing peptide synthesis procedures well known in the art. Preferred procedures useful in preparing the instant compounds include the solid phase method of Merrifield, J. Am. Chem. Soc. 85, 2149 (1963) as modified by Yamashiro and Li, Proc. Natl. Acad. Sci. U.S.A. 71, 4945 (1974). A particular preferred solid phase synthetic procedure is described by Li et al. Int. J. Pept. Pro. Res. 14, 242 (1981) which provides the fragment camel β-endorphin (7-31) to which the desired initial protected seven amino acids are added in reverse sequence, i.e., Ser, Thr, Met, Phe, Gly, Gly, Tyr. Analogous procedures substituting the needed known amino acids in the sequence of the β-endorphin moiety can be used to provide the desired human or porcine variants. Specific procedures for the solid phase synthesis of human β-endorphin (7-31), for example, are set forth in U.S. Pat. No. 4,116,950, which description is incorporated by reference herein.

N α-protection for all amino acids was by the Boc group and side-chain protection was as follows: Ser, O-Benzyl; Thr, O-benzyl; Glu, γ-benzyl ester; Lys, N ε-O-bromobenzyloxycarbonyl; Tyr, O-benzyloxycarbonyl. The preformed symmetrical anhydrides of the Boc-amino acids were prepared as described by Blake and Li, Int. J. Pept. Prot. Res. 7, 495 (1975).

The final protected peptide can be removed from the synthesis resin in a manner known per se such as by treatment with hydrofluoric acid preferably in the presence of anisole. Such treatment also serves to cleave off the side chain protecting groups.

Purification of the desired product is readily accomplished using known column chromatography procedures such as, for example, by use of a Sephadex G-10 column, followed by chromatography on carboxymethylcellulose and finally by partition chromatography on Sephadex G-50.

Characterization of the final product peptides is accomplished by amino acid analysis of acid hydrolysates and enzyme digests, paper electrophoresis and thin layer chromatography.

The compounds of the present invention are potent opiate agonists and thus are useful as analgesics, narcotic antagonists and anti-diarrhea agents.

They can be used as medicaments in the form of pharmaceutical preparations having direct or delayed liberation of the active ingredient which contain them in association with a compatible carrier material. This carrier material can be an organic or inorganic inert carrier material suitable for enteral, percutaneous or parenteral application such as water, gelatin, gum arabic, lactose, starch, magnesium stearate, talc, vegetable oils, polyalkylene glycols, petroleum jelly, etc. A preferred form suitable for parenteral administration involves preparation of a purified, lyophilized form of the active compound which is reconstituted prior to use by the addition of sterile, distilled water or saline.

If necessary, the pharmaceutical preparations can be sterilized and/or contain adjuvant substances such as preserving, stabilizing, wetting or emulsifying agents, salts for the variation of the osmotic pressure or substances acting as buffers.

The compounds of the present invention can be conveniently administered by the parenteral route preferably intravenously or intrathecally with a dosage in the range of about 0.25 mg to 15 mg per administration.

Also equivalent to the aforesaid β-endorphin analogs for the purposes of this invention are the pharmaceutically acceptable acid addition salts thereof. Such acid addition salts can be derived from a variety of inorganic and organic acids such as sulfuric, phosphoric, hydrochloric, hydrobromic, hydroiodic, nitric, sulfamic, citric, lactic, pyruvic, oxalic, maleic, succinic tartaric, cinnamic, acetic, trifluoroacetic, benzoic, salicylic, gluconic, ascorbic and related acids.

The following Examples serve to further illustrate the present invention.

EXAMPLE 1

[D-Ala$^2$,Phe$^3$,Gly$^4$,Tyr$^5$,Pro$^6$]$\beta_c$-endorphin

Synthesis of protected peptide resin corresponding to $\beta_c$-endorphin-(7-31) has been described by Li et al., Int. J. Peptide Prot. Res. 18, 242 (1981). The same synthetic procedures were used to complete the sequence corresponding to [D-Ala$^2$,Phe$^3$,Gly$^4$,Tyr$^5$,Pro$^6$]-$\beta_c$-endorphin. From 115 mg of starting Boc-Gln-resin (49 umol) there was obtained 0.32 g of final protected peptide polymer. This was treated in liquid HF (ca. 8 ml) in the presence of anisole (0.65 ml) for 90 min at 0°. After removal of HF the residue was mixed with 20% acetic acid (10 ml) and washed with three 10-ml portions of petroleum ether. The aqueous layer was filtered to remove resin and then passed through a Sephadex G-10 column (2.5×40 cm) in 20% acetic acid to yield 118 mg. This material was submitted to chromatography on carboxymethylcellulose as described previously Li et al. supra to yield 73 mg. Final purification was effected by partition chromatography on Sephadex G-50 in a 2.2×58 cm column with the solvent system 1-butanol:pyridine:0.6 M NH$_4$OAc (5:3:10); R$_f$ 0.6-0.7; yield, 46 mg according to the procedure of Yamashiro in *Hormonal Proteins and Peptides* IX pp. 25-107, (Academic Press, New York 1980).

Paper electrophoresis (50 μg samples) on Whatman 3 MM at pH 3.7 (pyridine acetate buffer) and at pH 6.7 (γ-collidine acetate buffer) for 4 h at 400 V gave a single spot for each (ninhydrin and Cl$_2$-tolidine detection) with R$_f$ values of 0.60 and 0.50, respectively, relative to lysine. Thin-layer chromatography (50 ug sample) on silica gel in 1-butanol pyridine:acetic acid:water (5:5:1:4) gave one spot with R$_f$ 0.53 (ninhydrin and Cl$_2$-tolidine detection).

Amino acid analysis of a 24-h HCl hydrolysate gave (theoretical values in parentheses):
Asp, 2.04 (2); Thr, 1.91 (2); Ser, 1.89 (2); Glu, 2.83 (3); Pro, 2.13 (2); Gly, 2.10 (2); Ala, 2.97 (3); Val, 1.00 (1); Ile, 1.15 (2); Leu, 2.14 (2); Tyr, 1.85 (2); Phe, 1.91 (2); His, 0.94 (1); Lys, 5.15 (5). The low value for Ile is accounted for by the acid resistant Ile-Ile moiety.

EXAMPLE 2

Bioassay

Analgesic Potency was estimated by the tail-flick method of D'Amour and Smith, J. Pharmacol. Exp. Ther. 72, 74 (1941) using groups of 8 mice per dose as described previously by Loh et al., Proc. Natl. Acad. Sci. USA 73, 2895 (1976).

Human $\beta$-endorphin, dermorphin, and morphine were assayed for analgesia in a mouse tail-flick test by the i.c.v. route, and dose-response curves were obtained. Parallelism between the curves for human $\beta$-endorphin and dermorphin suggest interaction at the same site. The dose-response curve of [D-Ala$^2$,Phe$^3$,Gly$^4$,Tyr$^5$,Pro$^6$]$\beta_c$-endorphin was compared with that of camel $\beta$-endorphin in the mouse tail-flick assay and it was observed that the analog is more active than camel $\beta$-endorphin.

The relative analgesic potencies of synthetic peptides are shown in Table 1. dermorphin is about 670 times as active as morphine, in good agreement with the value of 752 reported by Broccardo et al. Br. J. Pharmacol. 73, 625 (1981). Dermorphin is about 4.5 times more potent than human $\beta$-endorphin, while [D-Ala$^2$,Phe$^3$,Gly$^4$,Tyr$^5$,Pro$^6$]-$\beta_c$-endorphin is about 4.4 times as active. Thus, extension of the dermorphin sequence at the COOH-terminus with the $\beta_c$-endorphin-(8-31) sequence does not alter analgesic potency. On the other hand, the replacement of positions 1-7 of $\beta_c$-endorphin with the dermorphin sequence greatly increases the potency of camel $\beta$-endorphin. It is surprising that the drastic change in structure represented by [D-Ala$^2$,Phe$^3$,Gly$^4$,Tyr$^5$,Pro$^6$]-$\beta_c$-endorphin led to such a potent analgesic.

EXAMPLE 3

In analogy to the procedures employed in Example 1 and using human $\beta$-endorphin (7-31) whose preparation is described in U.S. Pat. No. 4,116,950, there is prepared [D-Ala$^2$,Phe$^3$,Gly$^4$,Tyr$^5$,Pro$^6$]-$\beta_h$-endorphin.

I claim:

1. Analogs of $\beta$-endorphin of the formula
[D-Ala$^2$,Phe$^3$,Gly$^4$,Tyr$^5$,Pro$^6$]-$\beta$-endorphin
and the pharmaceutically acceptable acid addition salts thereof.

2. The compound of claim 1 which is
[D-Ala$^2$,Phe$^3$,Gly$^4$,Tyr$^5$,Pro$^6$]-$\beta_c$-endorphin.

3. The compound of claim 1 which is
[D-Ala$^2$,Phe$^3$,Gly$^4$,Tyr$^5$,Pro$^6$]-$\beta_h$-endorphin.

* * * * *

UNITED STATES PATENT AND TRADEMARK OFFICE
CERTIFICATE OF CORRECTION

PATENT NO. : 4,422,968
DATED : December 27, 1983
INVENTOR(S) : CHOH HAO LI

It is certified that error appears in the above-identified patent and that said Letters Patent are hereby corrected as shown below:

Title page under UNITED STATES PATENT [19] , "Haoli" should be Hao Li

[75] Inventor: Choh "Haoli" should be Hao Li

Signed and Sealed this

Thirty-first Day of December 1985

[SEAL]

Attest:

Attesting Officer

DONALD J. QUIGG

Commissioner of Patents and Trademarks